US006318372B1

(12) United States Patent
Hiebert

(10) Patent No.: US 6,318,372 B1
(45) Date of Patent: Nov. 20, 2001

(54) VACUUM-ACTIVATED VETERINARY SURGICAL POSITIONING SYSTEM

(76) Inventor: Eugene Lloyd Hiebert, 3871 Comcomly Dr. SE., Salem, OR (US) 97306

(*) Notice: Subject to any disclaimer, the term of this patent is extended or adjusted under 35 U.S.C. 154(b) by 0 days.

(21) Appl. No.: 09/389,674

(22) Filed: Sep. 2, 1999

(51) Int. Cl.$^7$ ................................................. A61B 19/00
(52) U.S. Cl. ........................ 128/869; 128/870; 128/845
(58) Field of Search .................... 128/845, 846, 128/869, 870, 876; 5/624, 625, 82 R, 628

(56) References Cited

U.S. PATENT DOCUMENTS

| D. 362,913 | 10/1995 | Eisenberg et al. | D24/190 |
|---|---|---|---|
| 3,212,497 | 10/1965 | Dickinson | 128/87 |
| 3,762,404 | 10/1973 | Sakita | 128/78 |
| 4,234,982 | 11/1980 | Bez et al. | 5/455 |
| 4,657,003 | 4/1987 | Wirtz | 128/133 |
| 4,862,879 | 9/1989 | Coombs | 128/87 R |
| 4,885,811 | * 12/1989 | Hayes | 128/870 |
| 4,962,769 | 10/1990 | Garcia | 128/889 |
| 4,999,867 | 3/1991 | Toivio et al. | 5/455 |
| 5,121,756 | 6/1992 | Koledin | 128/870 |
| 5,154,185 | 10/1992 | Latimer et al. | 128/870 |
| 5,586,348 | 12/1996 | Toivio et al. | 5/710 |
| 5,621,934 | 4/1997 | Olkkonen et al. | 5/710 |
| 5,626,150 | 5/1997 | Johnson et al. | 128/870 |
| 5,634,222 | 6/1997 | Zwickey | 5/628 |
| 5,647,079 | 7/1997 | Hakamiun et al. | 5/713 |
| 5,659,908 | 8/1997 | Nishino | 5/676 |
| 5,906,205 | 5/1999 | Hiebert | 128/845 |

OTHER PUBLICATIONS

Schroer Manufacturing Company, Shor–line® catalog; "Vacu–Positioner" 4 pp., p. G1 ( 1987).
Schroer Manufacturing Company, Shore–line® catalog; "Vacu–Positioner" p. F20 (Sep. 1998).

* cited by examiner

*Primary Examiner*—Michael A. Brown
(74) *Attorney, Agent, or Firm*—Klarquist Sparkman LLP

(57) ABSTRACT

A vacuum activated veterinary surgical positioning system is disclosed for supporting and retaining the body of a four-legged animal in a selected position. The system includes a bag made of flexible, air impermeable material having top and bottom opposing walls air impermeably joined at their upper, lower and lateral edges. The bag has a width about equal to the sum of the width of the animal's trunk plus the widths of the lateral portions of the animal's trunk. The bag has a trunk portion with a length about the same as the length of the animal's trunk. The bag is extended in its center portion to provide a medically desirable support for the animal's head and neck. A charge of elastically deformable plastic beads is disposed within the bag. A valve communicating with the interior of the bag is provided for evacuating air therefrom to cause the beads to interengage to form a rigid structure and immobilize the animal's trunk in the selected position when the bag is firmly packed against the trunk. Finally, a strap is attached to each of the corners of the bag for attachment to each of the animal's legs to retain the leg in a desired position.

4 Claims, 2 Drawing Sheets

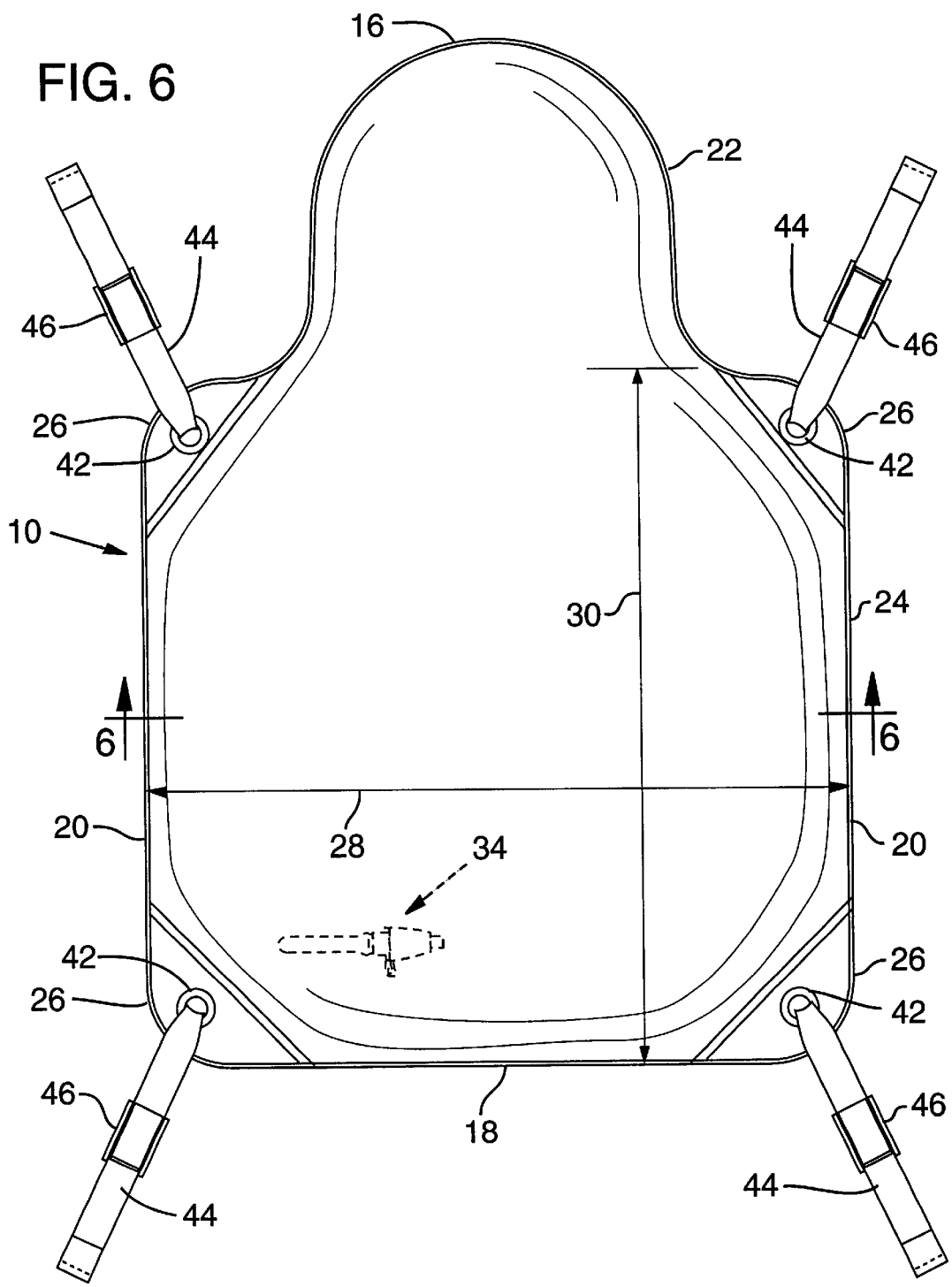
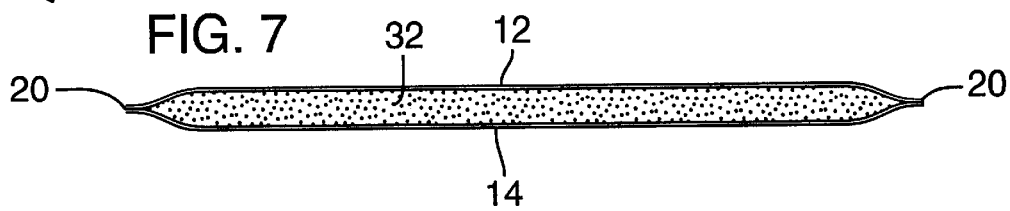

VACUUM-ACTIVATED VETERINARY SURGICAL POSITIONING SYSTEM

FIELD OF THE INVENTION

This invention relates to an improved positioning system for supporting, restraining and immobilizing a four-legged animal during medical treatment and during emergency transportation therefor.

BACKGROUND OF THE INVENTION

In my U.S. Pat. No. 5,906,205 I disclosed a vastly improved surgical positioning method and system for supporting the body of a human patient in a selected position and more particularly, in a selected lateral position wherein such support is especially challenging. The information in the aforesaid patent is herein expressly incorporated by reference.

It is self-evident that the similar support and restraining of four-legged animals pose additional challenges. Cats, dogs, sheep and alpacas often require such support and restraining during a variety of medical procedures, including their transportation to and from such procedures. The procedures include radiological examinations, pre-operative preparation, surgery in a variety of positions, and post-operative recovery procedures.

A support and restraining system must, of course, primarily maintain the animal securely in any desired position. It should conserve the animal's body heat, support the animal's head and neck, conform gently to the animal's body contours, and prevent pressure sores. The system desirably should be usable by the veterinary physician in a variety of locations—in the field, in a veterinary hospital, and in the veterinary office. The system should be able to achieve emergency fracture stabilization. Practically, the system should able to be easily cleaned.

The system should be obtainable in a variety of sizes to accommodate animals ranging in size from small puppies to alpacas. The entire system, including the various sized devices and necessary accessories, should be storable and transportable in a single container.

Vacuum-activated positioning devices are, of course, well known for use with human patients. The devices typically comprise a flexible air impervious bag containing small, elastically deformable particles or beads that consolidate into a rigid mass when the bag is evacuated. They have been well known since the Sakita, U.S. Pat. No. 3,762,404, issued Oct. 2, 1973. Devices of this type are typically filled with thousands of tiny, elastically deformable, generally spherical, plastic beads. When such a device is in the soft (unevacuated) condition, the beads are free to move around so that the device can be molded to the patient's body. When air is removed (using a vacuum source), atmospheric pressure forces the beads together into a solid mass, comfortably positioning, yet immobilizing the patient in the selected position. Allowing air back into the device returns it to its initial soft condition, ready for re-use.

Heretofore, there have not been many such devices of this type available for veterinary medical use. Schroer Manufacturing Company, Kansas City, Mo. 64108, has sold such a veterinary positioning device under its Shor-Line® brand. The device, known as its "Vacu-Positioner", fails to provide a support for the animal's head and neck. It also fails to provide strap means at each of the corners to retain the animal's legs in a desired position during the relevant procedures.

Adequate and proper support for the animal's head and neck is of particular importance. It should support the head and neck in a neutral position to prevent nerve injury to the neck and fore limbs. It should support the head to prevent pressure sores on the bony portion of the head during long surgical procedures. It should support the head and neck to prevent dislodgment of the endotracheal tube utilized during general anesthesia. It should provide stabilization of the head and neck during emergency transport to prevent further neurological injury. It should prevent heat loss during general anesthesia since the majority of the animal's body heat is transmitted through the head. It should allow for secure positioning of the head and neck during maxillo-facial, oral, nasal, cranial, auricular, cervical and opthalmological surgery. It must also allow for optimal positioning of the oropharynx to prevent post-operative aspiration of gastric contents.

The principal object of the present invention is thus to provide an improved vacuum actuated surgical positioning system that can be used with veterinary patients and that will achieve compliance with the requirements above set forth.

It is a further object of the present invention to provide such a system that is especially adapted for use with four-legged animals.

It is a still further object of the present invention to provide such a system that can be provided in a variety of sizes easily transported for use by the veterinary physician wherever needed.

SUMMARY OF THE INVENTION

My veterinary surgical positioning system achieves the foregoing objects according to the requirements above set forth. It comprises a bag made of flexible, air impermeable material having top and bottom opposing walls that are air impermeably joined at their upper, lower and lateral edges. The bag has a width equal to the sum of the width of a four-legged animal's trunk plus the widths of the trunk's lateral portions. At its lateral edges the bag has a length about the same as the length of the animal's trunk.

The bag is constructed such that the walls are extended centrally of their upper edges to provide the necessary support and thermal insulation for the animal's head and neck as hereinabove discussed.

A charge of elastically deformable beads is disposed within the bag. A valve is provided for communication with the interior of the bag for evacuating air therefrom, whereupon the beads in the bag interengage to form a rigid structure to support and immobilize the animal's trunk in a selected position when the bag is packed against the animal's trunk.

A strap is attached to at least one and, preferably, to each of the corners of the bag for attachment to a respective one of the animal's legs to retain the leg in a desired position during the relevant procedures.

My method comprises providing a system as aforesaid; placing the bag on a support; evenly distributing the beads within the bag; and placing the animal longitudinally in the center of the bag with the animal's head resting on the central extension. My method further comprises folding the lateral portions of the bag up against the sides of the animal's trunk while the animal is held in a selected position; and packing the lateral portions of the bag against the sides of the animal's trunk to accommodate the natural contours thereof. My method then comprises evacuating air from the interior of the bag while holding the animal in the selected position to cause the beads to interengage to form a rigid structure conforming to the contours of the animal's trunk. Finally, my method comprises attaching a strap at a corner of the bag to a respective one of the animal's legs to retain the leg in a desired position.

BRIEF DESCRIPTION OF THE DRAWINGS

FIG. 6 is a top plan view of the bag.

FIG. 7 is a cross-sectional view taken on line 7—7 of FIG. 6.

DETAILED DESCRIPTION

Figure 1:
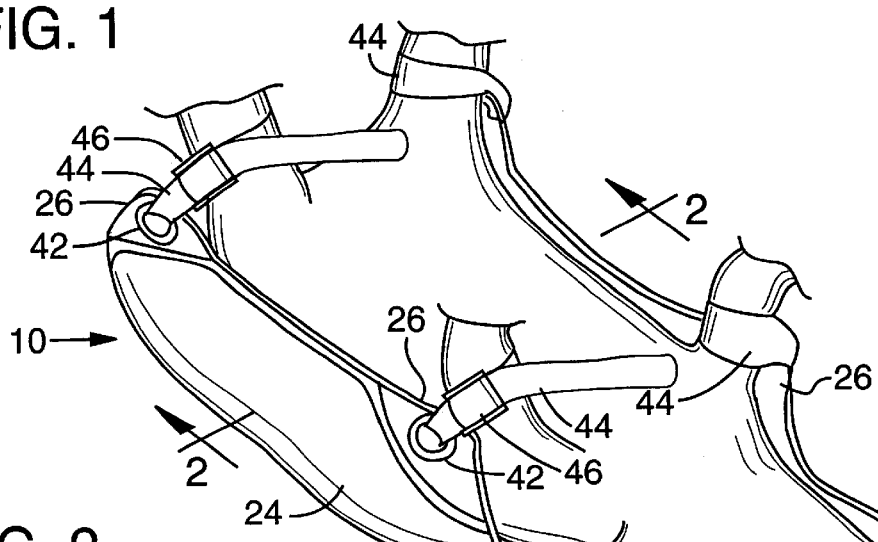
FIG. 1 is a perspective view of an animal on its back on the flexible, air impermeable bag with the corner straps attached to each of the animal's legs.

Referring to the drawings, my veterinary surgical positioning and retaining system comprises a generally flat bag 10 fabricated of flexible, air impermeable material. A suitable material is "Rocheaux Supreme" polyvinyl waterbed film, distributed by Rocheaux International, Inc., 1315 Watson Center Road, Carson, Calif. 90745, although other materials having similar properties may be used. The Rocheaux material has superior low temperature, tear, heat sealing and flexing qualities, also superior hydrostatic resistance that makes it particularly suitable for the present invention. It has good resilience, returning quickly to its prior conformation, thereby holding the veterinary patient more securely. It is mildew-, bacteria-, puncture-, and fire-resistant. Its physical properties are specifically set forth in my U.S. Pat. No. 5,906,205.

As shown in the drawings, the bag 10 comprises top and bottom opposing walls 12, 14 radio frequency welded together at their upper, lower and lateral edges 16, 18, 20 for strength and air tightness. The walls 12, 14 are extended generally in their center at their upper edges 16 to provide a central extension 22 for the animal's head and neck. The central extension 22 is sufficient to support the head and neck in a neutral position to prevent nerve injury to the neck and fore limbs. The extension 22 supports the head to prevent pressure sores on the bony portion of the head during long surgical procedures. The extension 22 supports the head and neck to prevent dislodgment of the endotracheal tube utilized during general anesthesia. The extension 22 further provides stabilization of the head and neck during emergency transport to prevent neurological injury.

The central extension 22 prevents heat loss during general anesthesia since the head transmits the majority of an animal's body heat loss. It also securely positions the head and neck during maxillo-facial, oral, nasal, cranial, auricular, cervical and opthalmological surgery Finally, the central extension 22 positions the oropharynx optimally to prevent any post-operative aspiration of gastric contents.

The trunk portion 24 of the bag has corners 26, as shown.

Preferably, the bag 10 is fabricated in four sizes as follows:

| SIZE | Overall Length in Inches | Overall Width in Inches | Length of Head Support, Inches | Width of Head Support, Inches | Corner Radius, Inches |
|---|---|---|---|---|---|
| A | 24 | 16 | 8 | 10 | 1-1/2 |
| B | 30 | 20 | 10 | 11 | 2-1/4 |
| C | 36 | 24 | 12 | 13 | 2-3/4 |
| D | 54 | 36 | 18 | 19 | 4-114 |

The size of the animal determines the size of the bag to be used. The width 28 of the bag should be generally equal to about the width of the animal's trunk plus twice the depth of the animal's trunk so the bag can be folded up about the trunk. The length 30 of the trunk portion 24 of the bag should be about the same as the length of the animal's trunk.

Before the walls 12, 14 are welded together as aforesaid, the bag is filled with a charge of elastically deformable plastic beads 32. The beads are preferably made of expanded plastic materials, such as polystyrene or polyvinyl chloride, because of their high mechanical strength, elastic deformability and low specific gravity. Beads 32 of expanded polystyrene are especially preferred. When the bag 10 is in the unevacuated condition, the beads 32 remain loose within the bag such that the lateral edges 20 can be easily moved or folded up along the sides of the animal's trunk to cradle and support the animal in the selected position.

Figure 2:
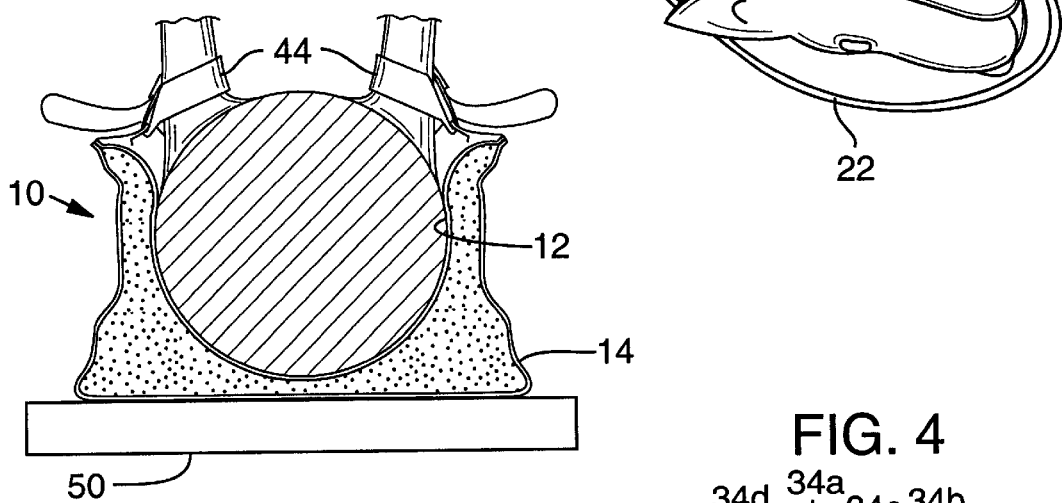
FIG. 2 is a cross-sectional view taken on line 2—2 of FIG. 1.
Figure 3:
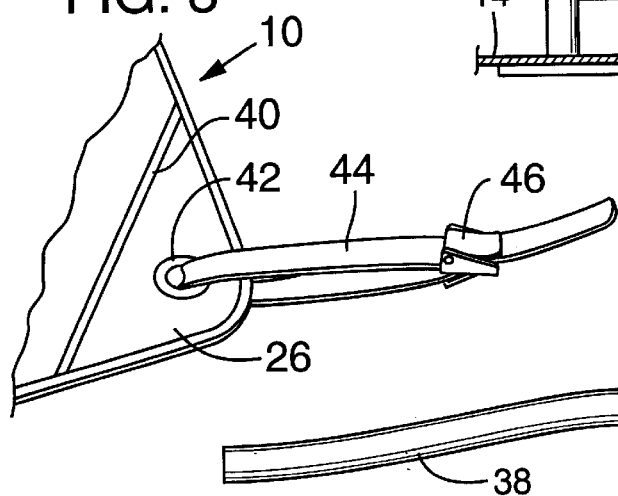
FIG. 3 is a perspective view to an enlarged scale of a corner of the bag illustrating the strap and buckle used to retain the animal's leg in the desired position.
Figure 4:
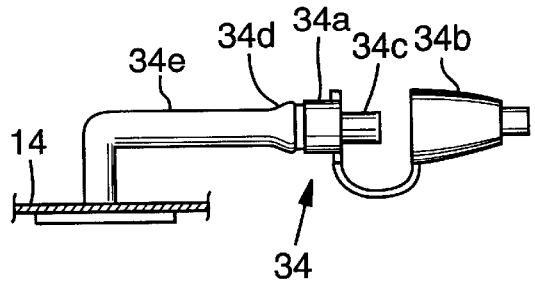
FIG. 4 is a side view of the valve used to evacuate air from the interior of the bag.
Figure 5:
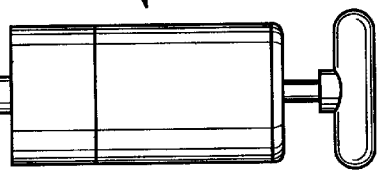
FIG. 5 is a side view of a manual pump and a hose that is connected to the valve used to evacuate air from the interior of the bag.

The bottom wall 14 of the bag 10 is provided with a valve 34 that communicates with the interior of the bag for evacuating air therefrom. See FIG. 4. A preferred valve suitable for this use is supplied by Colder Products Company, 1001 Westgate Drive, St. Paul, Minn. 55114, as its part number LSO 176-226. Other valves having similar properties can be used. As shown in FIG. 5, the valve 34 comprises male and female portions 34a, 34b. The total length of the valve is 3.04 inches. The male portion 34a comprises a valve stem 34c that protrudes from it when the valve 34 is closed. The proximal part 34d of the male portion 34a is inserted into a ⅜ inch inner diameter plastic tube 34e which is radio frequency welded to the bottom wall 14 for strength and air tightness. The female portion 34b is releasably placed over the male portion 34a to depress the valve stem 34c to open the valve 34 and allow ingress or egress of air. When a source of vacuum is attached to the female portion 34b, air is withdrawn from the interior of the bag 10. This causes the plastic beads 32 to be packed or to congregate into a tight configuration, conforming to the contours of the animal's trunk, as shown in FIGS. 1 and 2. When the female portion 34b is removed from the male portion 34a, the valve in the male portion 34a closes and no air can enter or exit the bag 10, thereby maintaining the acquired conformity of the bag about the animal's trunk.

When the animal is to be released, the female portion 34b of the valve 34 is placed over the male portion 34a. This opens the valve 34, thereby allowing air to enter the bag 10, disrupting the configuration of the plastic beads 32 and allowing the bag to become flat and flaccid. The valve 34 can also be opened by pressing the thumb nail down on the valve stem 34c of the male portion 34a. This also releases the vacuum.

The operating rooms of veterinary hospitals typically are not equipped with a source of vacuum pressure, and of course, such is not available in the field. Brice Tool & Stamping, Inc., 301 North Sullivan Street, Santa Ana, Calif. 92703 supplies a manual vacuum pump 36 suitable for this use as its Assembly No. 3220-00. The pump 36 weighs 1.5 pounds and has an overall length of 15.9 inches. It has a stroke length of 9.3 inches. It has an outside diameter of 2.5 inches and an inside diameter of 2.37 inches. It displaces 41 cubic inches per stroke. The pump 36 will draw a vacuum of 15 inches of mercury when twenty pounds of pulling force are applied to the handle.

The pump 36 is connectable to the female portion 34b of the valve 34 by a length of clear polyvinyl chloride braided hose 38, nominal size ⅜ inch×1B, supplied by Pacific Echo, Inc., 23540 Telo Avenue, Torrance, Calif. 90505, as its Spiralite® 410 PVC clear braided hose. This hose is effective in a temperature range of −10° F. to +130° F. and is suitable for conditions requiring see-through flow.

Each of the corners 26 of the bag is radio frequency welded along a diagonal line 40. A grommet 42 is inserted as shown to accommodate a polypropylene retention or restraint strap 44 provided with a cam buckle 46. American Cord & Webbing Co., Inc., 88 Century Drive, Woonsocket, R.I. 02895 supplies a strap 44 suitable for this use as its ACW Pattern No. 549. The strap 44 is preferably 16 inches long, black flat 0.75-inch wide braided polypropylene webbing, 0.050 inch thick, average breaking strength 360 lbs./inch, and is available with a Deirin® buckle having a pull strength of 25 lbs. Each of the straps 44 is placed around a respective leg of the animal and tightened using the buckle 46, as appropriate, to retain the animal's leg in a desired position after the bag 10 is evacuated to form the rigid supporting and restraining structure above described.

I provide a carrying case or duffel bag made of nylon large enough to accommodate the four sizes of bags as above set forth, also the vacuum pump 36 and tubing 38. In this manner the veterinary physician can transport the entire system with him wherever he or she may need it—in the field, in a veterinary hospital, or in the veterinary office.

METHOD OF THE INVENTION

In using the system of the invention, a bag 10 is chosen such that it is approximately the size required by the animal to be treated. The bag 10 is placed on a support 50 and is smoothed out such that the beads 32 are evenly distributed. The animal is then placed longitudinally in the center of the bag with its head resting on the central extension 22. The lateral sides of the bag 10 are then folded upwardly against the lateral portions of the animal's trunk while the animal is held in the selected position for the medical procedure to be performed. The lateral sides of the bag 10 are snugly packed against the sides of the animal's trunk to accommodate the natural contours thereof while the animal's head and neck rest on the central extension 22.

The vacuum pump 36 is connected to the valve 34 using the tubing 38. The pump 36 is activated to evacuate air from the interior of the bag 10 while the animal is held in the selected position with the sides of the bag 10 held snugly against the animal's trunk. Evacuation causes the beads 32 to interengage to form a rigid structure conforming to the contours of the animal's trunk. When satisfied with the achieved support, the pump 36 is detached from the valve 34. The bag 10 will then maintain its rigid conforming shape.

Each of the straps 44 is placed around the respective leg of the animal and the buckle 46 is tightened to retain the leg in the desired position.

When the medical procedure is finished, the straps 44 are loosened and air is reintroduced into the bag 10 to loosen the beads and allow the bag to become flat and flaccid. The animal can then be removed from the support and the bag 10 can be cleaned with a germicidal spray, as necessary.

My veterinary positioning system and method thus achieves compliance with all the requirements above set forth. Specifically, it can be used for pre-operative preparation, surgery in any position, post-operative recovery to prevent aspiration of fluids by the animal, radiological examinations, and emergency transportation. The system maintains the animal securely in any surgical position. The bag is very effective in conserving the animal's body heat during medical procedures. This is very important considering an animal's small mass to surface area ratio. Inasmuch as the evacuated bag conforms gently to the contours of the animal's trunk, the bag prevents pressure sores. The invention can be used in the veterinary office, in a veterinary hospital, and even out in the field. The manual vacuum pump makes the system easy to use in each of these locations. The invention is effective in emergency fracture stabilization. And the system is easily maintained inasmuch as it is easily cleaned.

Finally, inasmuch as I provide a series of bags in a range of sizes with a suitable carrying case, the invention will accommodate animals from puppies to alpacas.

While I have shown and described an embodiment of my invention, it is to be understood that the invention is not limited thereto, but is susceptible of numerous changes and modifications as will be apparent to those skilled in the art. I therefore do not want to be limited to the details shown and described herein, but intend to cover all changes and modifications encompassed by the scope of the following claims.

I claim:

1. A vacuum activated veterinary surgical positioning system for supporting and retaining the body of a four-legged animal in a selected position, comprising:

a bag made of flexible, air impermeable material having top and bottom opposing walls air impermeably joined at their edges, the bag comprising:

a generally rectangular portion suitable for supporting the trunk of a four-legged animal, the generally rectangular portion having corners at its upper and lower ends, the generally rectangular portion having a length generally equal to the length of the animal's trunk, the generally rectangular portion having a width generally equal to the width of the animal's trunk plus twice the depth of the animal's trunk, whereby the generally rectangular portion can be folded up about the animal's trunk to support the same, and an upper centrally disposed, extended portion for supporting the head and neck of the animal, the length of the extended portion being sufficient to support the animal's head, the width of the extended portion being substantially less than the width of the generally rectangular portion but sufficient to support the animal's head and neck, the interiors of the generally rectangular portion and the extended portion being wholly in communication with each other without compartmentalization;

a charge of elastically deformable beads comprising expanded plastic materials disposed within the bag, the beads remaining loose within the bag when the bag is in the unevacuated condition whereby the edges of the generally rectangular portion can be easily moved and folded up along the sides of the animal's trunk when the same is in the selected position;

a valve communicating with the interior of the bag for evacuating air therefrom, whereby upon evacuation of the air from within the bag, the beads in the generally rectangular and extended portions of the bag interengage to form a rigid structure to support and immobilize the animal's trunk in the selected position, while the extended portion supports and stabilizes the animal's head and neck in a neutral position; and a strap attached to each of the corners of the generally rectangular portion of the bag, each of the straps being adapted to encircle a respective leg of the animal to retain the same in a desired position after the bag is evacuated to form the rigid structure.

2. The positioning system of claim 1, wherein the elastically deformable beads comprise plastic materials selected from the group consisting of polystyrene and polyvinyl chloride.

3. The positioning system of claim 1, wherein the generally rectangular portion of the bag is substantially square when the bag is in the unevacuated condition.

4. The positioning system of claim 1, wherein the straps comprise a buckle to retain the animal's leg in the desired position.

\* \* \* \* \*